US009775778B2

(12) United States Patent
Qiu et al.

(10) Patent No.: US 9,775,778 B2
(45) Date of Patent: Oct. 3, 2017

(54) INTEGRATED MEDICINE MIXING INTERFACE

(75) Inventors: Yu Qiu, Chongqing (CN); Ke Li, Chongqing (CN); Yuan Yuan, Chongqing (CN); Hongyu Li, Chongqing (CN); Bing Zhou, Chongqing (CN); Liuying Zhao, Chongqing (CN)

(73) Assignee: CHONGQING LUMMY PHARMACEUTICAL CO., LTD, Chongqing (CN)

( * ) Notice: Subject to any disclaimer, the term of this patent is extended or adjusted under 35 U.S.C. 154(b) by 793 days.

(21) Appl. No.: 14/415,131

(22) PCT Filed: Aug. 2, 2012

(86) PCT No.: PCT/CN2012/079560

§ 371 (c)(1), (2), (4) Date: Jan. 15, 2015

(87) PCT Pub. No.: WO2013/067836

PCT Pub. Date: May 16, 2013

(65) Prior Publication Data

US 2015/0202120 A1 Jul. 23, 2015

(30) Foreign Application Priority Data

Nov. 11, 2011 (CN) .......................... 2011 1 0357048
Apr. 23, 2012 (CN) ..................... 2012 2 0173737 U

(51) Int. Cl.
*A61B 19/00* (2006.01)
*A61J 1/20* (2006.01)
(Continued)

(52) U.S. Cl.
CPC ............... *A61J 1/2089* (2013.01); *A61J 1/10* (2013.01); *A61J 1/1481* (2015.05); *A61J 1/2051* (2015.05);
(Continued)

(58) Field of Classification Search
CPC .......... A61J 1/10; A61J 1/1406; A61J 1/1481; A61J 1/2051; A61J 1/2089; A61J 1/201;
(Continued)

(56) References Cited

U.S. PATENT DOCUMENTS 8,585,674 B2 * 11/2013 Brandenburger ..... A61J 1/1406 604/403
2004/0199139 A1 10/2004 Fowles et al.

FOREIGN PATENT DOCUMENTS

CN 2843445 Y 12/2006
CN 2850611 Y 12/2006
(Continued)

OTHER PUBLICATIONS

International Search Report for PCT/CN2012/079560.
European Search Report for EP 12847291 dated May 23, 2016, 7 pages.

*Primary Examiner* — Philip R Wiest
(74) *Attorney, Agent, or Firm* — Kilpatrick Townsend & Stockton LLP

(57) ABSTRACT

An integrated medicine mixing interface comprising a medicine mixing mouth (1), hard double interfaces (2) and a medicine feed needle (3). The hard double interfaces (2) comprise a base (21), a medicine mixing interface (22) and an infusion interface (23). The medicine mixing mouth (1) and the medicine mixing interface (22) are integrated. When using the integrated medicine mixing interface, it is only necessary to weld the base (21) to the bag body of a soft infusion bag (11) and integrate the medicine mixing mouth (1) with the medicine mixing interface on the hard double
(Continued)

interfaces (2) without adopting a hose connection and an easily folding handle, which not only reduces hose installation location, but also avoids welding leakage brought about by hose welding defects. Moreover, the structure is simple and the costs are low.

15 Claims, 4 Drawing Sheets

(51) Int. Cl.
*A61J 1/10* (2006.01)
*A61J 1/14* (2006.01)
*B01F 13/00* (2006.01)

(52) U.S. Cl.
CPC ......... *B01F 13/0023* (2013.01); *A61J 1/2013* (2015.05); *A61J 1/2055* (2015.05); *B01F 2215/0032* (2013.01)

(58) Field of Classification Search
CPC .............. A61J 1/20553; B01F 13/0023; B01F 2215/0032
USPC .................................................. 604/403–416
See application file for complete search history.

(56) References Cited

FOREIGN PATENT DOCUMENTS

| | | | |
|---|---|---|---|
| CN | 2915101 | Y | 6/2007 |
| CN | 102178602 | A | 9/2011 |
| CN | 102499888 | A | 6/2012 |
| CN | 202314384 | U | 7/2012 |
| JP | 5-337163 | A | 12/1993 |
| JP | H07275324 | | 10/1995 |
| JP | 8-141049 | A | 6/1996 |
| WO | 91/11152 | | 8/1991 |
| WO | 2007/149960 | A2 | 12/2007 |

* cited by examiner

INTEGRATED MEDICINE MIXING INTERFACE

The present application is the national phase of International Application No. PCT/CN2012/079560, titled "INTEGRATED MEDICINE MIXING INTERFACE", filed on Aug. 2, 2012, which claims the benefits of priorities to Chinese Patent Application No. 201110357048.4, filed on Nov. 11, 2011, and Chinese Patent Application No. 201220173737.X, filed on Apr. 23, 2012, all of which applications are incorporated herein in their entireties by this reference.

TECHNICAL FIELD

The present invention relates to a medical appliance, and particularly to double hard interfaces with a medicine mixing nozzle.

BACKGROUND

In clinical treatment of diseases, it is often required to provide transfusion to a patient or directly inject medicine into a body by intravenous drip. The medicine is usually stored within a transfusion soft bag, and the input or output of the medicine within the transfusion soft bag is typically achieved by a double hard interface with a medicine mixing nozzle.

In the prior art, the double hard interfaces with the medicine mixing nozzle mainly include a base, a medicine mixing snapping body, a syringe body, a hose, a easy-to-break handle and a medicine feeding needle. A medicine mixing interface and a transfusion interface are provided on the base, and the medicine mixing interface extends out of the base and has a hollow cylindrical structure. The transfusion interface extends out of the base and has a hollow cylindrical structure. The medicine mixing snapping body has a hollow cylindrical structure. The medicine feeding needle is provided within the medicine mixing snapping body. A lower end surface of the medicine mixing snapping body is sealed from the outer wall of the medicine feeding needle, and the syringe body is located at the lower end surface of the medicine mixing snapping body. The hose has one end sleeved onto the medicine mixing interface and welded together with the medicine mixing interface; and has the other end sleeved onto the syringe body and welded together with the syringe body. The easy-to-break handle is mounted within the hose and is mainly configured to block the passage between the medicine feeding needle and the medicine mixing interface. When mixing the medicine, it is necessary to break off the easy-to-break handle, and then the passage between the medicine feeding needle and the medicine mixing interface can be communicated.

The double hard interfaces with the medicine mixing nozzle described above have the following disadvantages: 1, the medicine mixing nozzle and the medicine mixing interface on the double hard interfaces are required to be connected via the hose, and the hose has one end sleeved onto the medicine mixing interface on the double hard interfaces and welded together with the medicine mixing interface, and has the other end sleeved onto the syringe body and welded together with the syringe body, which not only increases positions for installing the hose, but also increases the welding portions, increases the probability of leakage at the welding portions during mixing medicine; 2, the medicine mixing nozzle is communicated with the medicine mixing interface on the double hard interfaces by the hose, the hose may be easily broken off at the welding portions at low temperature (e.g. a temperature below zero) because of the limitation of the material adopted for making the hose, thus resulting in leakage during mixing medicine; 3, in a case that the medicine mixing nozzle having the structure described above is communicated with the medicine mixing interface on the double hard interfaces by the hose, an easy-to-break handle is further required to be installed within the hose, which increases the process difficulty and working hours consumed, and also probably to lower the product yield.

SUMMARY OF THE INVENTION

In view of the disadvantages of the prior art described above, an integrated medicine mixing interface is provided according to the present invention, which has a simple structure and low cost without adopting an easy-to-break handle and a hose, and avoids leakage in mixing medicine caused by welding.

In order to address the technical problems mentioned above, the following technical solutions are employed in the present invention.

An integrated medicine mixing interface, includes a medicine mixing nozzle, double hard interfaces and a medicine feeding needle, the double hard interfaces include a base, a medicine mixing interface and a transfusion interface, wherein the medicine mixing nozzle and the medicine mixing interface are integrally formed.

As a preferred solution of the present invention, the medicine feeding needle is a cross-shaped needle, an inner wall of a medicine mixing passage formed by the medicine mixing nozzle integrated with the medicine mixing interface is provided with an annular rubber cushion I, and a lower portion of the cross-shaped needle is snapped into an inner hole of the annular rubber cushion I, and a base of the cross-shaped needle is located within a medicine mixing snapping body of the medicine mixing nozzle.

As another preferred solution of the present invention, a diaphragm for sealing the medicine mixing passage is provided within the medicine mixing interface.

As yet another preferred solution of the present invention, welding lines are uniformly arranged all over the outer wall of the base.

As an improved solution of the present invention, both ends of the base extend outwardly to form thin sheets with the thickness tapering.

As another improved solution of the present invention, the medicine mixing snapping body of the medicine mixing nozzle has a hollow cylindrical structure, and at least two barb-shaped slip-proof buckles for preventing a medicine container from loosening are symmetrically provided on an inner wall of the medicine mixing snapping body.

As yet another improved solution of the present invention, a sealing cover is provided on an upper end of the medicine mixing snapping body of the medicine mixing nozzle.

As a further improved solution of the present invention, an annular rubber cushion II is provided within the medicine mixing snapping body and above the base of the medicine feeding needle, and the annular rubber cushion II is sleeved outside the medicine feeding needle.

As a still further improved solution of the present invention, the annular rubber cushion II is located between the base and the slip-proof buckles.

The advantage effects of the present invention is that, when using the integrated medicine mixing interface, it is only required to weld the base to the bag body of the transfusion soft bag and integrate the medicine mixing nozzle with the medicine mixing interface on the double hard interfaces without adopting a hose connection or an easy-to-break handle, which not only reduces hose installation locations, but also avoids leakage from weld seam caused by the disadvantages of hose welding, moreover, the structure is simple and the cost is low.

1—medicine mixing nozzle; 2—double hard interface; 21—base; 22—medicine mixing interface; 23—transfusion interface; 3—medicine feeding needle; 4—annular rubber cushion I; 5—base; 6—medicine mixing snapping body; 7—welding lines; 8—thin sheet; 9—slip-proof buckle; 10—sealing cover; 11—transfusion soft bag; 12—medicine container; 13—annular rubber cushion II; 14—diaphragm.

DETAILED EMBODIMENTS

The present invention is described in detail hereinafter in conjunction with the drawings and specific embodiments.

Figure 1:
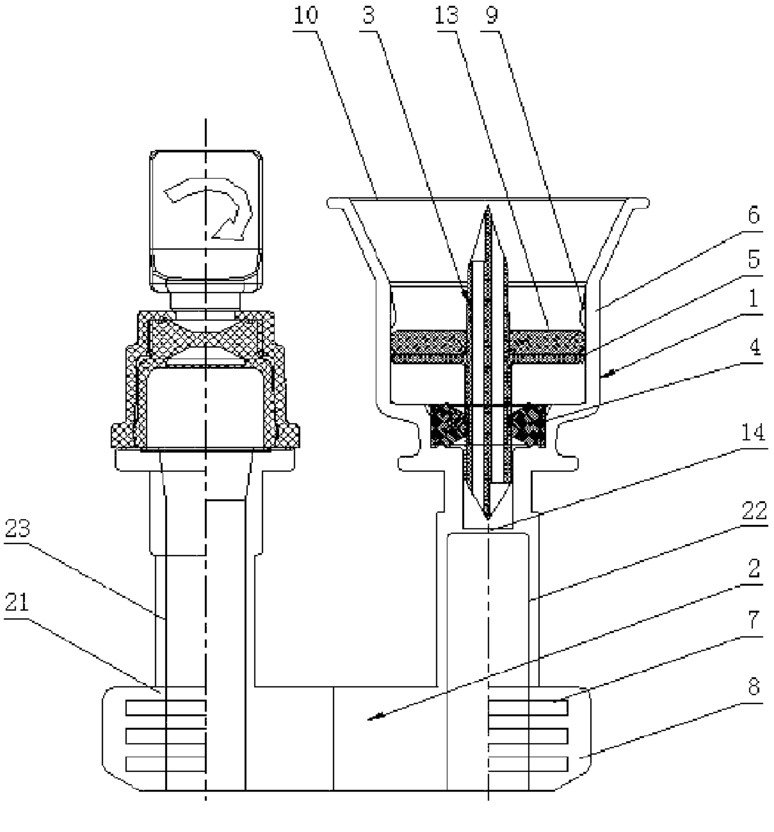
FIG. 1 is a schematic view showing the structure of an integrated medicine mixing interface.
Figure 2:
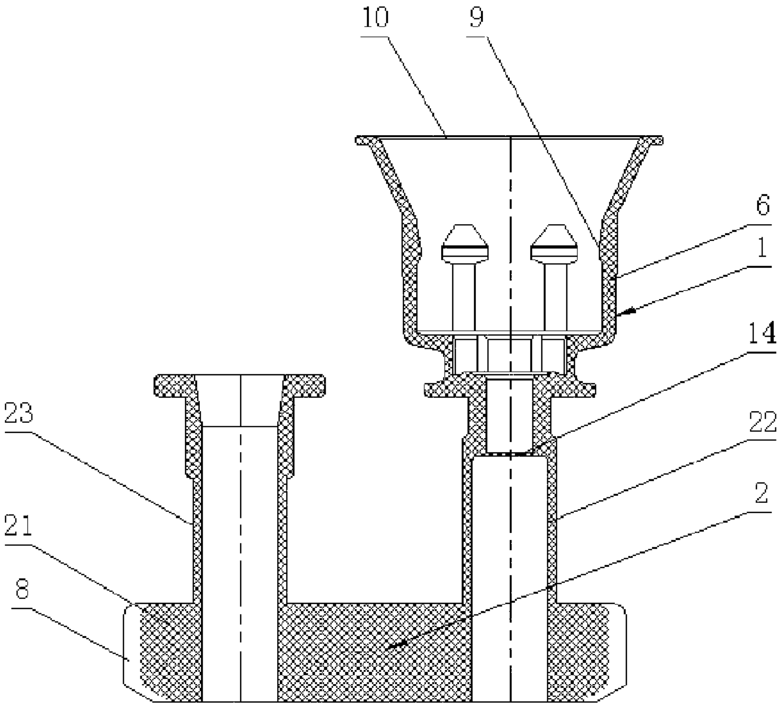
FIG. 2 is a schematic view showing the structure of a medicine mixing nozzle integrated with double hard interfaces.
Figure 3:
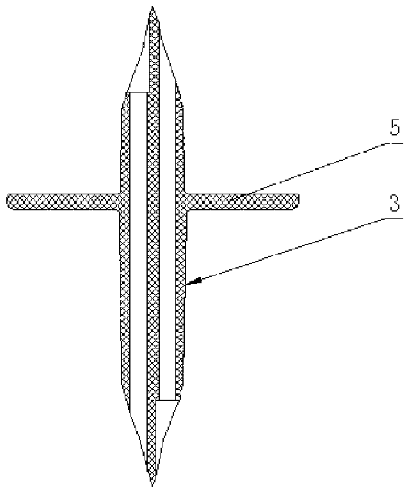
FIG. 3 is a schematic view showing the structure of a medicine feeding needle.

As shown in FIGS. 1, 2 and 3, an integrated medicine mixing interface includes a medicine mixing nozzle 1, double hard interface 2 and a medicine feeding needle 3. The double hard interface 2 include a base 21, a medicine mixing interface 22 and a transfusion interface 23. The medicine nozzle 1 and the medicine mixing interface 22 are integrally formed.

Figure 4:
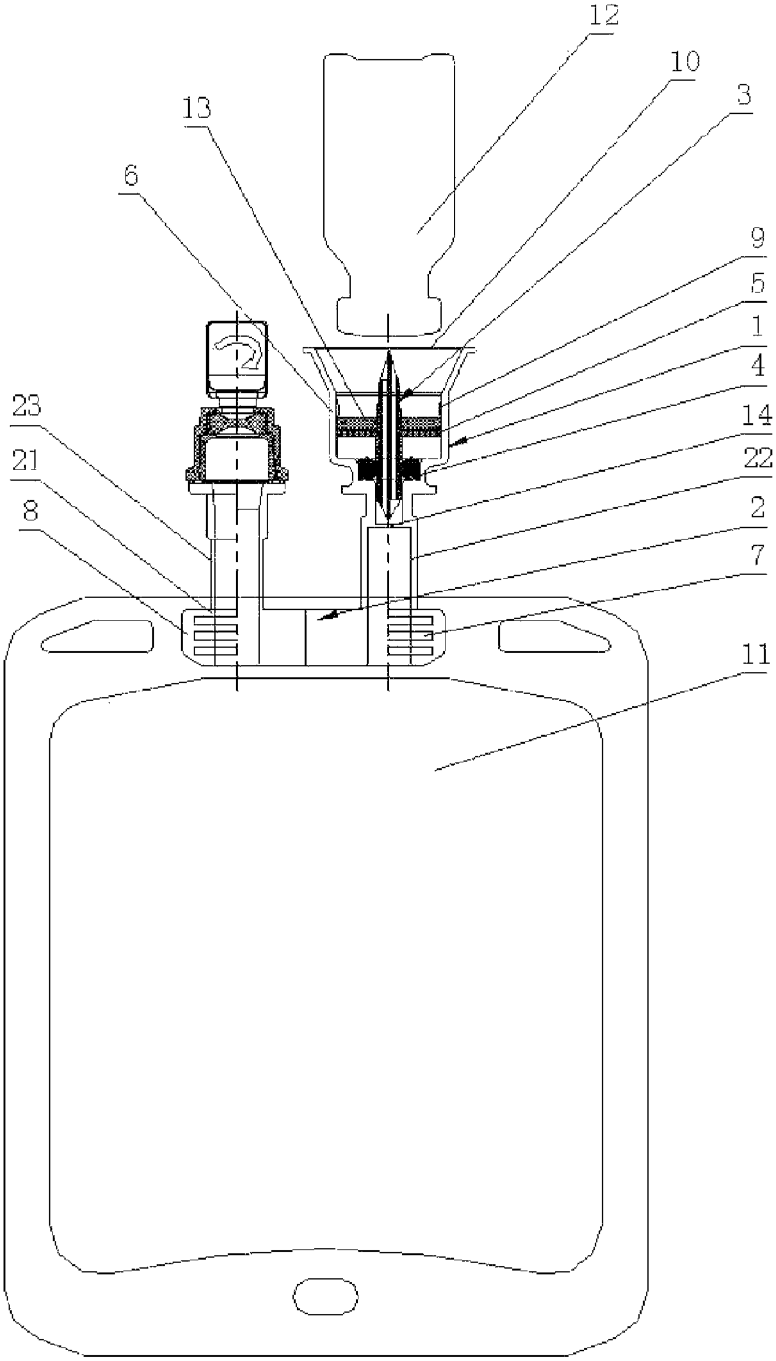
FIG. 4 is a schematic view showing the structure of the integrated medicine mixing interface before use.
Figure 5:
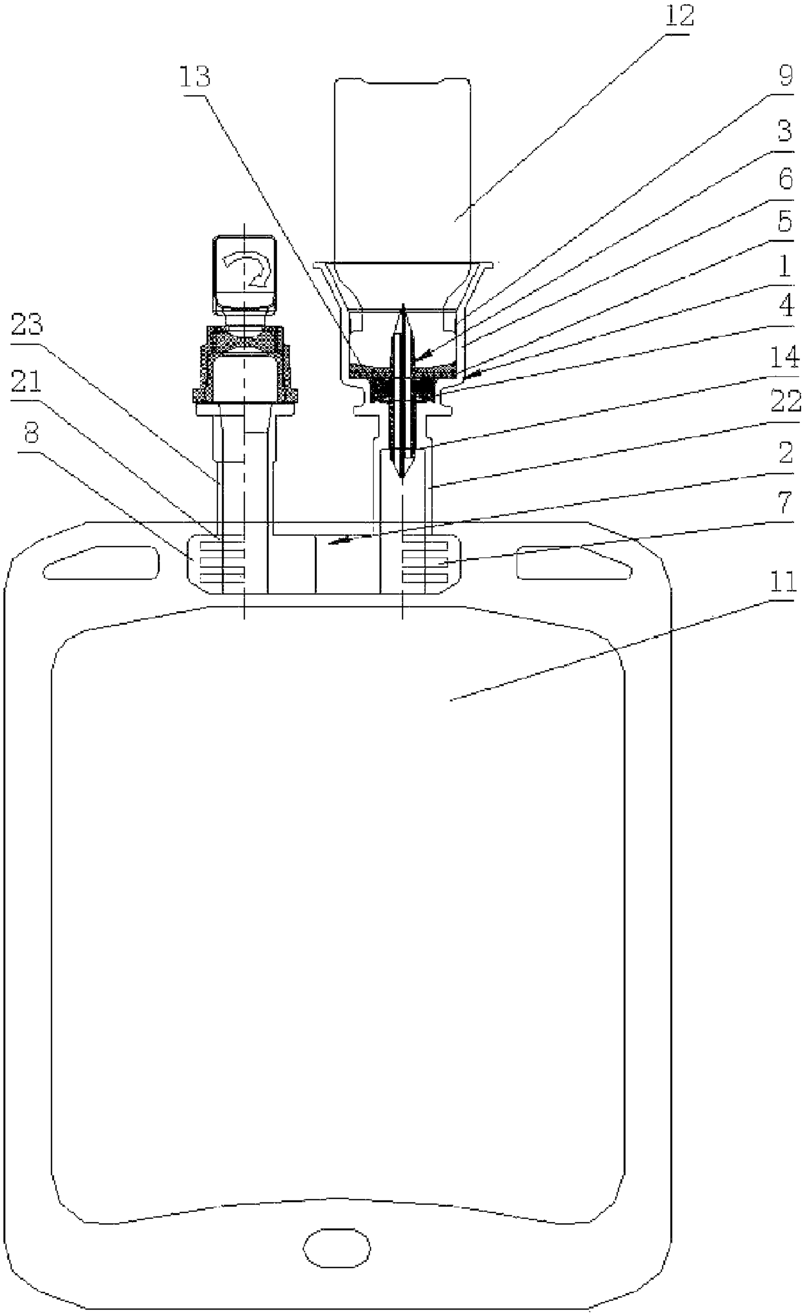
FIG. 5 is a schematic view showing the structure of the integrated medicine mixing interface in use.

The medicine feeding needle 3 is a cross-shaped needle (i.e., medicine feeding double needles, a cutting plane in an axis direction of the medicine feeding needle has a "cross-shaped" structure), the upper and lower needle tips of the medicine feeding needle 3 are both of a conical structure, and three needle holes are evenly distributed on a conical surface of the conical structure. The inner wall of a medicine mixing passage formed by the medicine mixing nozzle 1 integrated with the medicine mixing interface 22 is provide with an annular rubber cushion I4, and a lower portion of the cross-shaped needle is snapped into an inner hole of the annular rubber cushion I4, and a base 5 of the cross-shaped needle is located within a medicine mixing snapping body 6 of the medicine mixing nozzle 1. A diaphragm 14 for sealing the medicine mixing passage is provided within the medicine mixing interface 22. Before the base 21 of the double hard interfaces 2 is welded onto the transfusion soft bag 11 to perform medicine mixing (as shown in FIG. 4), the diaphragm 14 may block up the medicine mixing passage, such that the transfusion solvent in the transfusion soft bag 11 is kept sealed and does not contact with the medicine feeding needle 3, which avoids that the transfusion solvent is poured into the medicine mixing snapping body 6 through the medicine feeding needle 3 to cause leakage, and thus not only strictly ensuring the volume of the transfusion solvent in the transfusion soft bag 11, but also avoiding contamination before use. When the diaphragm 14 is punctured by the medicine feeding needle 3, the medicine mixing interface 22 is communicated with the medicine feeding needle 3, thus allowing the transfusion solvent to flow into a medicine container to achieve medicine mixing (as shown in FIG. 5). At this time, the annular rubber cushion I4 replaces the diaphragm 14, which may not only isolate the transfusion solvent to prevent the transfusion solvent from contacting the outside, but also limit the transfusion solution to flow into a medicine container 12 only through the medicine feeding needle 3. Thus, the arrangement of the diaphragm 14 strictly controls the order of opening the medicine mixing passage, and ensures the safety and sanitation in the medicine mixing process. Furthermore, the diaphragm 14 and the medicine mixing interface 22 can be integrated, which is easily implemented by simply process and will not increase the economical burden to customers because of the low cost of the material.

Welding lines 7 are uniformly arranged all over the outer wall of the base 21 (four welding lines are uniformly arranged all over the outer wall of the base 21 according to this example). A projection of the base 21 on its cross section has a boat-shaped structure, and both ends of the base 21 in the boat-shaped structure extend outwardly to form thin sheets 8 with the thickness tapering. In a state that heat welding is performed, the base 21 is more reliably welded to a bag port of the transfusion soft bag 11 by the welding lines 7 on the base 21, and the effect of the sealing between the base 21 and the transfusion soft bag 11 is much better. Moreover, the thin sheets 8 on both sides of the base 21 and the bag port of the transfusion soft bag 11 can be melt together more quickly, which not only increases the welding speed, but also enhances the effect of the sealing between the base 21 and the transfusion soft bag 11.

The medicine mixing snapping body 6 has a hollow cylindrical structure. At least two barb-shaped slip-proof buckle 9 for preventing the medicine container from loosening are symmetrically provided on the inner wall of the medicine mixing snapping body 6. Six slip-proof buckle 9 are symmetrically arranged on the inner wall of the medicine mixing snapping body 6 according to this example. After the medicine container 12 is snapped into the medicine mixing snapping body 6, under the hindering effect of the slip-proof buckle 9, the medicine container 12 may be effectively prevented from escaping or loosening from the medicine mixing snapping body 6 in the opposite direction.

A sealing cover 10 is provided on an upper end of the medicine mixing snapping body 6. Before use, the sealing cover 10 can not only ensure that the medicine mixing snapping body 6, the medicine feeding needle 3 within the medicine mixing snapping body 6 and the medicine mixing passage within the double hard interfaces 2 are in a sealed state, to allow the medicine mixing snapping body 6, the medicine feeding needle 3 within the medicine mixing snapping body 6 and the medicine mixing passage within the double hard interfaces 2 to have good cleanliness before use, but also effectively preserve the sharpness of the upper needle of the medicine feeding needle and the inner structure of the medicine mixing snapping body 6, avoiding the damage during transportation. When in use, it is simply required to remove the sealing cover 10, which is convenient and ensures the cleanliness of the medicine mixing snapping body 6, the medicine feeding needle 3 within the medicine mixing snapping body 6 and the medicine mixing passage within the double hard interfaces 2.

An annular rubber cushion II 13 is provided within the medicine mixing snapping body 6 and above the base 5 of the medicine feeding needle 3. The annular rubber cushion II 13 is sleeved outside the medicine feeding needle 3, and is located between the base 5 and the slip-proof buckle 9. Since the annular rubber cushion II 13 sleeved outside the medicine feeding needle 3 is provided within the medicine mixing snapping body 6 and above the base 5 of the medicine feeding needle 3, and the annular rubber cushion II 13 has good elasticity, when the medicine container 12 is snapped into the medicine mixing snapping body 6 (as shown in FIG. 5), the medicine container 12 may be prevented from loosening by the annular rubber cushion II 13 and the slip-proof buckle 9 on the medicine mixing snapping body 6. The position at which the medicine container 12 is connected to the medicine mixing snapping body 6 by being inserted is sealed completely by the annular rubber cushion II 13, which prevents medicine leakage from occurring during medicine mixing, and strictly ensures the absolute air-tightness in the medicine container after the medicine mixing, and avoids the risk of bacterial infections Using the integrated medicine mixing interface may include welding the base 21 onto the bag port of the transfusion soft bag 11, and snapping a bottom portion of the medicine feeding needle into the inner hole of the annular rubber cushion I4, as shown in FIG. 4. Mixing the medicine may include removing the sealing cover 10, snapping the medicine container 12 into the medicine mixing snapping body 6, and then pushing the medicine container 12 downwardly, to allow the medicine feeding needle 3 to be push downwardly while a sealing plug of the medicine container 12 is punctured by the top portion of the medicine feeding needle 3, such that the diaphragm 14 within the medicine mixing interface 22 is punctured by the bottom portion of the medicine feeding needle 3, and the base 5 of the medicine feeding needle 3 is finally moved to the bottom portion of the medicine mixing snapping body 6, thereby the medicine container 12 is communicated with the transfusion soft bag 11, as shown in FIG. 5.

Finally, it should be noted that the examples described above is merely to illustrate the technical solution of the present invention and not for limitations, although the present invention is described in detail with reference to preferred examples, it should be understood to an ordinary skilled in the art that the technical solution of the present invention can be modified or substituted equivalently without departing from the spirit and the scope of the technical solution of the present invention, which should be encompassed in the scope defined by the claims of the present invention.

The invention claimed is:

1. An integrated medicine mixing interface, comprising a medicine mixing nozzle (1), double hard interface (2) and a medicine feeding needle (3), the double hard interface (2) comprise a base (21), a medicine mixing interface (22) and a transfusion interface (23), characterized in that the medicine mixing nozzle (1) and the medicine mixing interface (22) are integrally formed;

wherein the medicine feeding needle (3) is a cross-shaped needle, an inner wall of a medicine mixing passage formed by the medicine mixing nozzle (1) integrated with the medicine mixing interface (22) is provided with a first annular rubber cushion (4), and a lower portion of the cross-shaped needle is snapped into an inner hole of the first annular rubber cushion (4), and a base (5) of the cross-shaped needle is located within a medicine mixing snapping body (6) of the medicine mixing nozzle (1).

2. The integrated medicine mixing interface according to claim 1, characterized in that a diaphragm (14) for sealing the medicine mixing passage is provided within the medicine mixing interface (22).

3. The integrated medicine mixing interface according to claim 1, characterized in that welding lines (7) are uniformly arranged all over an outer wall of the base (21).

4. The integrated medicine mixing interface according to claim 2, characterized in that welding lines (7) are uniformly arranged all over an outer wall of the base (21).

5. The integrated medicine mixing interface according to claim 1, characterized in that both ends of the base (21) extend outwardly to form thin sheets (8) with the thickness tapering.

6. The integrated medicine mixing interface according to claim 1, characterized in that both ends of the base (21) extend outwardly to form thin sheets (8) with the thickness tapering.

7. The integrated medicine mixing interface according to claim 2, characterized in that both ends of the base (21) extend outwardly to form thin sheets (8) with the thickness tapering.

8. The integrated medicine mixing interface according to claim 1, characterized in that the medicine mixing snapping body (6) of the medicine mixing nozzle (1) has a hollow cylindrical structure, and at least two barb-shaped slip-proof buckles (9) for preventing a medicine container from loosening are symmetrically provided on the inner wall of the medicine mixing snapping body (6).

9. The integrated medicine mixing interface according to claim 2, characterized in that the medicine mixing snapping body (6) of the medicine mixing nozzle (1) has a hollow cylindrical structure, and at least two barb-shaped slip-proof buckles (9) for preventing a medicine container from loosening are symmetrically provided on the inner wall of the medicine mixing snapping body (6).

10. The integrated medicine mixing interface according to claim 1, characterized in that a sealing cover (10) is provided on an upper end of the medicine mixing snapping body (6) of the medicine mixing nozzle (1).

11. The integrated medicine mixing interface according to claim 2, characterized in that a sealing cover (10) is provided on an upper end of the medicine mixing snapping body (6) of the medicine mixing nozzle (1).

12. The integrated medicine mixing interface according to claim 1 characterized in that a second annular rubber cushion (13) is provided within the medicine mixing snapping body (6) and above the base (5) of the medicine feeding needle (3), and the second annular rubber cushion (13) is sleeved outside the medicine feeding needle (3).

13. The integrated medicine mixing interface according to claim 2, characterized in that a second annular rubber cushion (13) is provided within the medicine mixing snapping body (6) and above the base (5) of the medicine feeding needle (3), and the second annular rubber cushion (13) is sleeved outside the medicine feeding needle (3).

14. The integrated medicine mixing interface according to claim 12, characterized in that the second annular rubber cushion (13) is located between the base (5) and the slip-proof buckle (9).

15. The integrated medicine mixing interface according to claim 13, characterized in that the second annular rubber cushion (13) is located between the base (5) and the slip-proof buckle (9).

* * * * *